(12) United States Patent
Sullivan et al.

(10) Patent No.: US 7,904,152 B2
(45) Date of Patent: Mar. 8, 2011

(54) EXTERNAL DEFIBRILLATOR WITH CHARGE ADVISORY ALGORITHM

(75) Inventors: Joseph L. Sullivan, Kirklnad, WA (US);
Patrick F. Kelly, Edmonds, WA (US);
Richard C. Nova, Kirkland, WA (US);
James W. Taylor, Sammamish, WA (US)

(73) Assignee: Physio-Control, Inc., Redmond, WA (US)

( * ) Notice: Subject to any disclaimer, the term of this patent is extended or adjusted under 35 U.S.C. 154(b) by 1107 days.

(21) Appl. No.: 11/008,876

(22) Filed: Dec. 9, 2004

(65) Prior Publication Data
US 2006/0129190 A1      Jun. 15, 2006

(51) Int. Cl.
*A61N 1/39* (2006.01)
(52) U.S. Cl. ............................ 607/5; 607/14
(58) Field of Classification Search .............. 607/4, 607/5, 14; 600/515–518
See application file for complete search history.

(56) References Cited

U.S. PATENT DOCUMENTS

| | | | |
|---|---|---|---|
| 5,097,830 A * | 3/1992 | Eikefjord et al. ............... | 607/8 |
| 5,111,813 A * | 5/1992 | Charbonnier et al. ........... | 607/8 |
| 5,179,945 A * | 1/1993 | Van Hofwegen et al. ....... | 607/5 |
| 5,191,884 A * | 3/1993 | Gilli et al. ....................... | 607/5 |
| 5,391,187 A * | 2/1995 | Freeman ........................ | 607/5 |
| 5,423,863 A * | 6/1995 | Felblinger et al. .............. | 607/5 |
| 5,496,349 A * | 3/1996 | Campbell et al. ............... | 607/5 |
| 5,607,454 A * | 3/1997 | Cameron et al. ................ | 607/5 |
| 5,700,281 A * | 12/1997 | Brewer et al. ................... | 607/5 |
| 5,797,969 A | 8/1998 | Olson et al. | |
| 5,817,132 A * | 10/1998 | Karagueuzian et al. ......... | 607/5 |
| 6,005,370 A * | 12/1999 | Gustavson et al. .......... | 320/137 |
| 6,029,084 A | 2/2000 | Long et al. | |
| 6,029,085 A * | 2/2000 | Olson et al. ..................... | 607/5 |
| 6,241,751 B1 * | 6/2001 | Morgan et al. ................. | 607/8 |
| 6,289,243 B1 * | 9/2001 | Lin et al. ........................ | 607/5 |
| 6,304,773 B1 * | 10/2001 | Taylor et al. ................ | 600/515 |
| 6,553,251 B1 | 4/2003 | Lahdesmaki | |

(Continued)

OTHER PUBLICATIONS

Zhu, Y.-S.; Thakor, N.V., "Detection of ventricular fibrillation by sequential testing", Sep. 25-28, 1988, Computers in Cardiology 1988. Proceedings, p. 325-328.*

(Continued)

*Primary Examiner*—Niketa I Patel
*Assistant Examiner*—Rex Holmes
(74) *Attorney, Agent, or Firm*—Shumaker & Sieffert, P.A.

(57) ABSTRACT

A method of delivering electrical therapy to a patient by a medical device includes activating the medical device and performing a first analysis of a first set of data signals sensed by the medical device. If the first analysis shows the first set of data signals meets a first criterion, then charging of an energy delivery circuit is commenced upon completion of the first analysis. A second analysis of a second set of data signals from the patient is performed, and if the second analysis determines that the second set of data signals meet a second criterion, the therapy is delivered. The steps of performing the first analysis and performing the second analysis may be begun at substantially the same time. The step of charging may overlap in time with the step of performing a second analysis. The medical device may be an external defibrillator and the therapy may be a defibrillating shock.

19 Claims, 2 Drawing Sheets

U.S. PATENT DOCUMENTS 6,553,257 B2    4/2003   Snyder et al.
6,658,290 B1 *  12/2003  Lin et al. ..................... 607/5
6,754,526 B2 *  6/2004   Daynes et al. ............... 607/5
7,027,863 B1 *  4/2006   Prutchi et al. ................ 607/5
7,242,979 B1 *  7/2007   Kelly et al. .................. 607/5

OTHER PUBLICATIONS

Tchoudovski et al., "New approach in developing of the algorithms for resuscitation assistance", Engineering in Medicine and Biology Society, 2004. EMBC 2004. Conference Proceedings. 26th Annual International Conference of the, vol. 1, 2004 p. 956-959 vol. 2.*

* cited by examiner

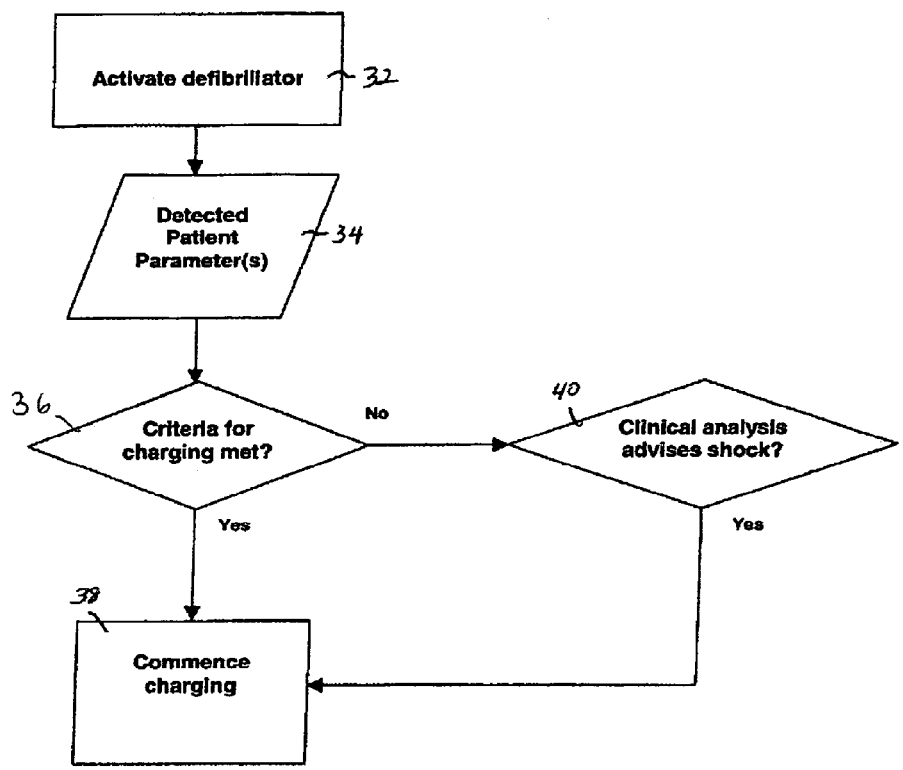
Figure 2
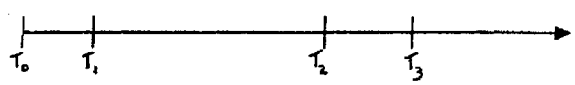
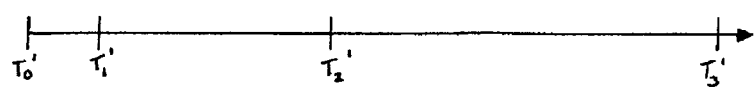

EXTERNAL DEFIBRILLATOR WITH CHARGE ADVISORY ALGORITHM

BACKGROUND OF THE INVENTION

1. Field of the Invention

The present invention relates generally to external defibrillators, and particularly to charging systems and algorithms for external defibrillators.

2. Technical Background

Sudden Cardiac Arrest (SCA) is a condition in which the heart exhibits a life-threatening abnormal rhythm, or arrhythmia. The most common arrhythmia is Ventricular Fibrillation (VF). When in VF, the heart's rhythm is so chaotic that the heart merely quivers, and is unable to pump blood to the body and brain. This chaotic rhythm is generally referred to as fibrillation. A victim in SCA first loses his or her pulse, then consciousness, and finally the ability to breath. These events happen in a matter of seconds.

An effective treatment for SCA is to deliver an electrical shock using a device called an external defibrillator to defibrillate the heart. Voltage stored by the external defibrillator is applied across the patient's heart by means of electrodes or paddles place on the victim's body, such as the victim's chest, resulting in an electrical current flow through the heart. The brief pulse of electrical current is provided to halt the fibrillation, giving the heart a chance to start beating with a normal rhythm. This delivering of the electrical shock, which is intended to return the heart to normal rhythm, is called defibrillation.

Survival rates for SCA are the highest when defibrillation is conducted within the first few minutes after onset of an arrhythmia, and the person has the best chance of survival if the defibrillation shock is given within the first three minutes of the person's collapse. One study has shown that the chances of resuscitating an individual suffering SCA are reduced by about 7% to about 10% with each minute that lapses between onset of SCA and application of the defibrillation shock. Therefore, rate of survival for SCA victims average less than 2% when defibrillation is delayed ten minutes or more.

There are several types of external defibrillators, including manual defibrillators, which are generally used by medical personnel, and automated external defibrillators, commonly known by the acronym AED, which are designed for use by laypersons. Typically an AED is a small, portable device that analyzes the heart's rhythm and if the analysis determines that a defibrillating shock is advisable, either prompts the user to deliver a defibrillation shock or delivers a defibrillation shock without user interaction. Once a typical AED is activated, it can guide the user through each step of the defibrillation process by providing instructions in the form of aural or visual prompts.

Commercially available AED's analyze the patient's heart rhythm and charge the energy storage capacitor before a defibrillating shock can be delivered to the patient. This is done using a decision-making algorithm commonly referred to as a shock advisory algorithm. Current commercially available defibrillators analyze the electrocardiogram (ECG) first to determine if the patient's heart is in a condition where delivery of a defibrillating shock is advisable, and after this analysis is done, charge if a shock is recommended. Typically, a shock advisory algorithm may take from about five to about 8 or more seconds to analyze, and the capacitor in a typical AED typically takes about 8 to about 10 or more seconds to charge up in preparation for delivery of a defibrillating shock. Time delays such as this have a negative impact on patient survival and should be minimized; the amount of time required for a defibrillator to get ready to deliver should be kept as short as possible.

Several approaches to reducing the time to shock have been proposed. One approach is to design device hardware so as to minimize the charging time. Unfortunately, this can raise manufacturing costs. Another approach is to commence charge of the defibrillator upon turning the device on. If the shock advisory analysis indicates that the patient requires a shock, then the device is ready to deliver the energy. But, if the analysis indicates that no shock is required, then the device will internally dump the stored charge. This results in a waste of energy that can result in increase cost of operation due to increased need for battery replacement. There also is concern about the potential for accidental delivery of energy since the charge will become available whenever the device is activated, whether needed for therapy or not.

SUMMARY OF THE INVENTION

One aspect of the present invention is a method of delivering electrical therapy to a patient by a medical device, including the steps of activating the medical device; performing a first analysis of a first set of data signals sensed by the medical device; if the first analysis shows the first set of data signals meets a first criterion, then commencing charging of an energy delivery circuit upon completion of the first analysis; performing a second analysis of a second set of data signals from the patient; and if the second analysis determines that the second set of data signals meet a second criterion, delivering the therapy. The steps of performing the first analysis and performing the second analysis may be begun at substantially the same time. The step of charging may overlap in time with the step of performing a second analysis. The medical device may be an external defibrillator and the therapy may be a defibrillating shock In another aspect of the invention, the first criterion indicates a degree of probability that the second analysis will result in delivery of the therapy.

In another aspect of the invention, the first set of data signals includes a patient physiological parameter, such as, for example, data signals indicative of the patient's cardiac activity. These may include, for example, ECG signals.

In another aspect of the invention, the first criterion includes a criterion indicative of attachment of electrodes to the patient.

In another aspect of the invention, the second set of data signals includes ECG signals.

In another aspect of the invention, the charging step may include charging the energy delivery device to a first charge level, and may further comprise the step of, after performing the second analysis, charging the energy storage device from the first level up to the charge level at which the device is capable of delivering the therapy.

In another aspect of the invention, the charging step may include charging the energy delivery device at a first rate of charge, and further comprise the steps of performing a third analysis of a third set of data signals sensed by the medical device, if the third analysis shows the third set of data signals meets a third criterion, increasing the rate of charge.

In another embodiment of the invention, a method for preparing a defibrillator for delivery of defibrillating therapy to a patient may include activating the defibrillator; prior to determining whether therapy delivery is advisable based on patient condition, determining whether the probability that defibrillating therapy will be delivered to the patient is at least a predetermined level; if the probability level is determined to be at least the predetermined level, commencing charging of an energy delivery circuit upon completion of the determination; and determining whether therapy delivery is advisable based on patient condition.

In another embodiment of the invention, an external defibrillator includes a sensor which senses data indicative of a patients' physiological condition; therapy delivery circuitry capable of being electrically charged; and a processor which analyses the data and directs the charging of the therapy deliver circuitry to commence upon a determination that the data indicates a predetermined probability that defibrillation therapy will be delivered.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

BRIEF DESCRIPTION OF THE DRAWINGS

FIG. 2 is a flow chart of a charge advisory analysis process of an embodiment of the invention.

FIG. 3 is a timing diagram for a first scenario of use of the embodiment of FIG. 2; and FIG. 4 is a timing diagram for a second scenario of use of the embodiment of FIG. 2.

DETAILED DESCRIPTION OF THE PREFERRED EMBODIMENTS

Figure 1:
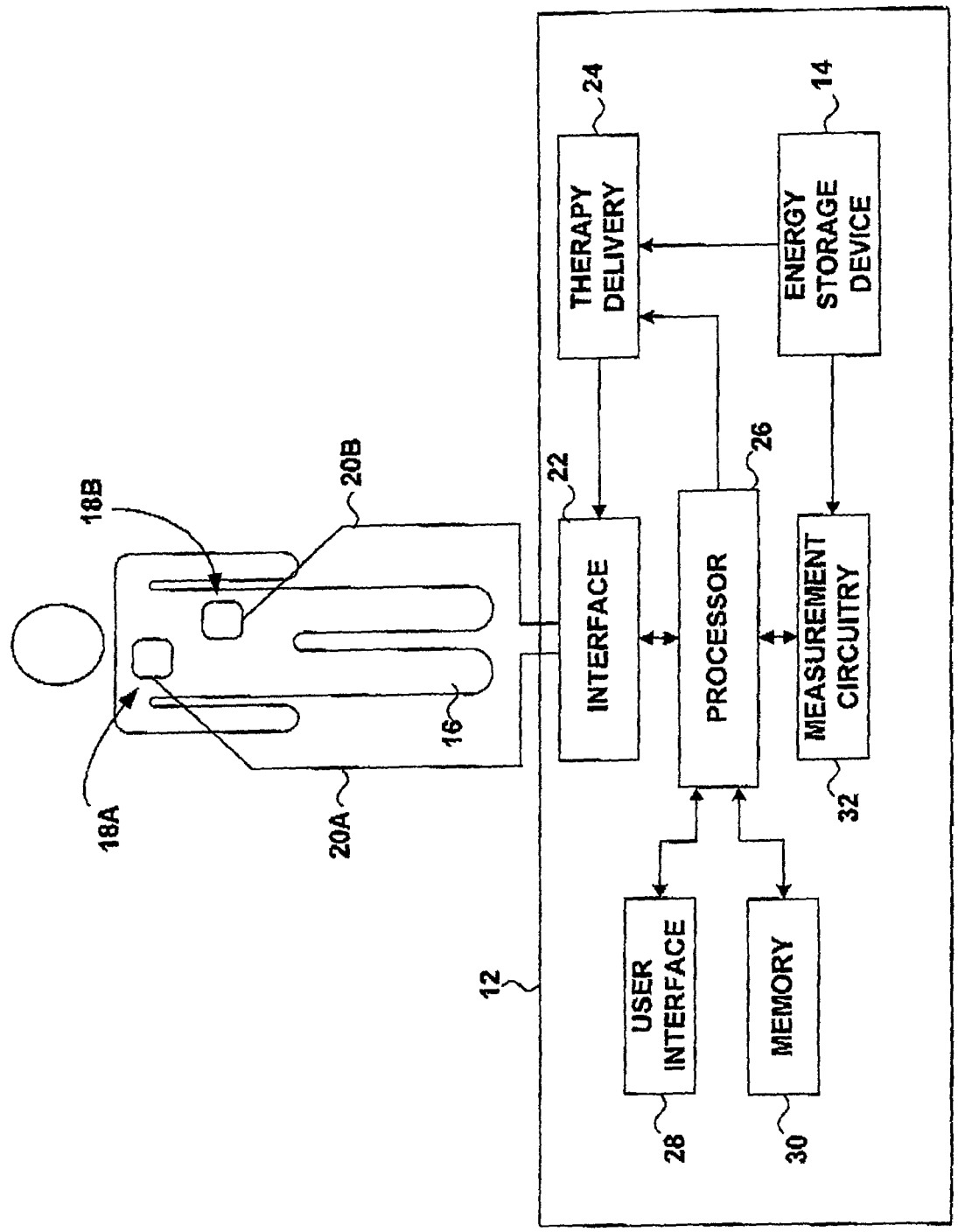
FIG. 1 is a schematic representation of an external defibrillator according to an embodiment of the invention.

Reference will now be made in detail to the present preferred embodiments of the invention, an example of which is illustrated in the accompanying drawings. Wherever possible, the same reference numbers will be used throughout the drawings to refer to the same or like parts. An exemplary embodiment of the medical device of the present invention is shown in FIG. 1, and is designated generally by reference numeral 18.

In FIG. 1, defibrillator 12 is shown coupled to a patient 16 by electrodes 18A and 18B (collectively "electrodes 18"). Electrodes 18 may include hand-held electrode paddles or adhesive electrode pads placed on the skin of patient 16. Electrodes 18 are coupled to defibrillator 12 via respective conductors 20A and 20B (collectively "conductors 20") and an interface 22. In a typical application, interface 22 includes a receptacle, and conductors 20 plug into the receptacle.

Interface 22 includes a switch (not shown in FIG. 1) that, when activated, couples therapy delivery circuitry 24 to electrodes 18 for delivery of energy to patient 16 via electrodes 18 in the form of a defibrillation shock. The switch may be of conventional design and may be formed, for example, of electrically operated relays. Alternatively, the switch may comprise an arrangement of solid-state devices such as silicon-controlled rectifiers or insulated gate bipolar transistors.

Therapy delivery circuitry 24 includes components, such as one or more capacitors, that store the energy to be delivered to patient 16 as a defibrillation shock. Before a defibrillation shock may be delivered to patient 16, these energy storage components are charged by charging circuitry, such as a flyback charger, that transfers energy from energy storage device 14 such as a battery to the components. A processor 26 directs the charging circuitry to charge the energy storage components to a selected voltage level that is determined based on a selected energy level for the defibrillation shock to be delivered to patient 16.

Defibrillator 12 may be a manual defibrillator or an AED. Where defibrillator 12 is a manual defibrillator, a caregiver using defibrillator 12 may select an energy level for each defibrillation shock delivered to patient 12. Processor 26 may receive the selection made by the caregiver via a user interface 28, which may include input devices, such as a keypad and various buttons or dials, and output devices, such as various indicator lights, a cathode ray tube (CRT), light emitting diode (LED), or liquid crystal display (LCD) screen, and a speaker. Where defibrillator 12 is an AED, processor 26 may select an energy level based on protocol stored in a memory 30 and the number of defibrillation shocks already delivered to patient 16. The protocol may define a preprogrammed progression of energy levels and numbers of shocks to be delivered at each energy level.

When the energy stored by therapy delivery circuitry 24 reaches the desired energy level, processor 26 controls user interface 28 to provide an indication to the caregiver that defibrillator 12 is ready to deliver a defibrillation shock to patient 16, such as an indicator light or a voice prompt. The defibrillation shock may be delivered manually or automatically. In a manual defibrillator and some AEDs, the user may direct processor 26 to deliver the defibrillation shock via user interface 28 by, for example pressing a button. In some other AEDs, the processor 26 will automatically cause delivery of the defibrillating shock without further user interaction. In either case, processor 26 activates the switches of interface 22 to electrically connect therapy delivery circuit 24 to electrodes 18, and thereby deliver the defibrillation shock to patient 16.

Processor 26 may perform other functions as well, such as monitoring electrical activity of the heart of patient 16 sensed via electrodes 18. Processor 26 may determine whether the heart of patient 16 is fibrillating based upon the sensed electrical activity in order to determine whether a defibrillation shock should be delivered to patient 16. Where a defibrillation shock has already been delivered, processor 26 may evaluate the efficacy of the delivered defibrillation shock by determining if the heart is still fibrillating in order to determine whether an additional defibrillation shock is warranted. Processor 26 may automatically deliver defibrillation shocks based on these determinations, or may advise the caregiver of these determinations via user interface 28.

Processor 26 may display an electrocardiogram (ECG) that reflects the sensed electrical activity via user interface 28. Further, processor 26 may control delivery of other types of therapy to patient 16 via electrodes 18, such as cardioversion or pacing therapy. Where defibrillator 12 is more fully featured, e.g., a manual paramedic or hospital defibrillator, defibrillator 12 may also include additional sensors (not shown) coupled to processor 26, such as sensors to measure blood oxygen saturation, temperature, blood pressure, and the amount of carbon dioxide in the air inhaled or exhaled by patient 16.

Processor 26 may, for example, include one or more of a microprocessor, digital signal processor (DSP), application specific integrated circuit (ASIC), field programmable gate array (FPGA), or other logic circuitry. In addition to various values, look-up tables, or equations described above, memory 30 may include program instructions that cause processor 26 to perform the functions attributed to processor 26 herein. Memory 30 may include any of a variety of solid state, magnetic or optical media, such as random access memory (RAM), read-only memory (ROM), CD-ROM, magnetic disk, electrically erasable programmable ROM (EEPROM), or flash memory.

In an embodiment of the invention, processor 26 will perform a charge advisory analysis that will determine whether to commence charging the one or more capacitors in the therapy delivery circuitry prior to the determination by the shock advisory algorithm of whether delivery of a shock is advised. In some embodiments, this charge advisory analysis may also determine the rate at which the charging is performed. A process for the charge advisory analysis is illustrated in the flowchart of FIG. 2. In the illustrated embodiment, after the defibrillator is turned on in a first step 32, the defibrillator provides data on sensed parameters to processor 26 in a second step 34. These parameters may include the patient's physiological parameters such as ECG, or device parameters indicative of some condition of the defibrillator 12 such as electrode impedance or user interaction with the defibrillator 12, or a combination of patient parameters and device parameters. If the sensed parameters meet criteria that would indicate some probability that a charge will be needed, then the processor would, in step 38, direct the energy storage device 14 to commence charging the therapy delivery circuitry 24. If the sensed parameters do not meet the charging criteria, then charging would not commence at that point in time. If, however, in step 40, the clinical analysis results in shock being advised, then charging would be commenced at completion of the clinical determination that shock is advised.

The charge advisory analysis may use relatively simple criteria for the charge decision. In one embodiment, the processor 26 will analyze a short segment of ECG and begin charging if all of the following criteria are met: 1) no QRS complexes are detected, 2) a flat line is not detected, and 3) the electrodes are attached to a patient. This analysis can be done in a small fraction of the time needed for the clinical analysis to be completed. Other criteria that would indicate a desired probability that a charge will be needed may, of course, be used in alternative embodiments of the invention. The desired degree of probability may be low. In determining the desired degree of probability level for a particular application, one may wish to weigh the desirability of commencing charging prior to a Shock Advised determination against that of avoiding charging where no shock will be advised, so as to preserve battery power and avoid any other deleterious effects of having charged up a defibrillator where no shock is advised.

In some applications, it may be desirable to commence charging if there is simply a non-zero probability that a shock will be advised. In an embodiment suitable for such an application, the parameter detected in step 34 would be electrode impedance, and the criteria for charging in step 36 would be whether the electrode impendence is within a range that would indicate the electrodes are attached to the patient 16. In this embodiment, after the defibrillator is turned on, it measures the electrode impedance to see if the electrodes are attached to a patient. Electrode impedance within a specified range, typically between 10 to 300 ohms, would be generally reliable indication that the electrodes 18 have been applied to the patient 16. Impedance outside this range would indicate that the electrodes 18 are not connected to a patient. Connection of electrodes to a patient would indicate a non-zero probability that a shock will be needed.

If the charge analysis indicates electrodes are not attached to a patient, then the defibrillator would not begin charging. The charge advisory analysis could be repeated until either the electrodes are attached to a patient or the defibrillator is turned off.

FIGS. 3 and 4 schematically illustrate the timing involved in two different scenarios in which embodiments of the invention are used. In both of these figures, the horizontal arrow represents progression in time. In FIG. 3, the defibrillator is activated at $T_0$. The charge advisory analysis is performed from $T_0$ to $T_1$. In the scenario shown in FIG. 3, the charge advisory analysis results in a determination that charging should be commenced, and charging is commenced approximately at time $T_1$. The clinical shock advisory analysis is performed from $T_0$ to $T_2$. At $T_2$, the shock advisory analysis determines a shock is advised, and so charging is continued until it is completed at $T_3$.

In the scenario shown in FIG. 4, the defibrillator is activated at $T_0'$. The charge advisory analysis is performed from $T_0'$ to $T_1'$. In the scenario shown in FIG. 4, a charge advisory analysis does not result in a determination that charging should be commenced, and charging is not commenced at time $T_1'$. This would be the case where the sensed parameters input into the charging decision do not meet the chosen criteria. The clinical shock advisory analysis is performed from $T_0'$ to $T_2'$. At $T_2'$, the shock advisory analysis determines a shock is advised, and so charging commences at approximately $T_2'$ and continues until it is completed at $T_3'$. The time it takes to charge the defibrillator for both scenarios would be substantially equal, i.e., $(T_3-T_1)=(T_3'-T_2')$. It will be noted, however, that the time from activation to the point where the defibrillator is fully charged and ready for delivery of shock in the scenario of FIG. 3, $(T_3-T_0)$ is substantially less than the corresponding time period in the scenario of FIG. 4, $(T_3'-T_0')$. Timing from activation of a defibrillator until readiness for shock delivery for a defibrillator that does not employ a charge advisory analysis according to an embodiment of the invention would be substantially the same as in the FIG. 4 scenario. If, for a defibrillator 12 employing a charge advisory analysis according to the invention, charging criteria are chosen so that, in most cases a determination to commence charging will be made prior to the shock advisory algorithm's determination that shock is advisable, then there will be a significant time saving in preparation for shock delivery in most cases where shock is advised.

In another alternative embodiment, a charge advisory analysis process is capable of providing a determination of whether charging should be commenced based on sensed parameters indicative of the probability of whether a shock will be advised, with an increasing confidence level over time. In an illustrative embodiment, this could be done by analyzing a first segment of a patient ECG and rendering a preliminary decision based on that analysis. A second segment of the ECG subsequent to the first segment could then be analyzed. If the two analyses agree, then one would have an increased confidence that the initial determination was correct. Similarly, additional segments could be analyzed on a continuous basis, providing increased confidence over time.

The progressive output of the charge advisory analysis in this embodiment could be used to provide intelligent control of the defibrillator capacitor charger. For example, the capacitor charger could be turned on at a first charge rate when the first Charge Advised determination is made. If a second Charge Advised determination agrees, then the charge rate could be increased. Finally, if the Shock Advisory Algorithm provides a shock advised decision before the capacitor is fully charged, then the charge rate would be increased to its maximum level. Another example of how charging could be controlled would be to charge the capacitor to a first charge level if an initial Charge Advised determination is made, and then charge to a second level if a second Charge Advised determination is made. This process of making progressive charge advisability determinations and charging to progressively higher levels may be repeated. If the Shock Advisory Algorithm advises that shock delivery is advised, charge would be completed, if it had not already been completed.

This progressive control of the capacitor charger provides a couple of benefits. One benefit is a reduced risk of capacitor charger noise artifact appearing on the ECG signal, which is one of the possible drawbacks of charging while an ECG analysis is performed. The other benefit is the reduced likelihood that the energy will be wasted.

This invention proposes a method of reducing the shock time delay while at the same time reducing the risk of wasted energy through unnecessary charging, reducing the hazard of having energy available when it is not required and minimizing the effect of charging artifact on the signal analysis. This invention proposes a method and device in which clinical analysis algorithms may operate, providing timely assessment of the patient status, and correctly preparing the device to support a patient in the most rapid fashion possible.

In the embodiments described above, the charging criterion is chosen to result in a Charging Advised determination in cases where a desired likelihood or probability that a shock will be advised is met. The parameters upon which this determination is made may include any of a signal such as ECG, or any of subset of similar signals giving a measure of cardiac activity, including, for example, ECG from multiple sites, transthoracic impedance, electric field plethysmography, photoplethysmography, cardiokymographic, ballistocardiographic, or acoustic plethysmography.

Data on the state of the defibrillator or how a user is interacting with a defibrillator may be used to make a determination of whether the desired level of probability has been met. These may include, for example, whether the user has applied the electrodes to the patient, or other operator actions such as connecting the electrodes to the defibrillator, opening the electrode pouch, removing the electrodes from the pouch, removing the backing material from the electrodes, or performing CPR on the patient It will be apparent to those skilled in the art that various modifications and variations can be made to the present invention without departing from the spirit and scope of the invention. Thus, it is intended that the present invention covers the modifications and variations of this invention provided they come within the scope of the appended claims and their equivalents.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

What is claimed is:

1. A method for delivery of electrical therapy to a patient by a medical device comprising:
   activating the medical device;
   performing a first analysis of a first set of data signals from the patient sensed by the medical device;
   if the first analysis shows that the first set of data signals meets a first criterion, commencing charging of an energy storage device upon completion of the first analysis;
   performing a second analysis of a second set of data signals from the patient regardless of the outcome of the first analysis; and
   if the second analysis determines that the second set of data signals meet a second criterion different from the first criterion, charging the energy storage device upon completion of the second analysis to a charge level at which the device is capable of delivering the therapy and delivering the therapy regardless of the outcome of the first analysis,
   wherein the first criterion indicates a degree of probability that the second analysis will result in delivery of the therapy.

2. The method of claim 1 wherein the steps of performing the first analysis and performing the second analysis are begun at substantially the same time.

3. The method of claim 2 wherein the step of charging of an energy storage device upon completion of the first analysis overlaps in time with the step of performing the second analysis.

4. The method of claim 1 wherein the medical device is an external defibrillator and the therapy is a defibrillating shock.

5. The method of claim 1 wherein the first set of data signals includes a patient physiological parameter.

6. The method of claim 5 wherein the first set of data signals includes data signals indicative of the patient's cardiac activity.

7. The method of claim 6 wherein the first set of data signals includes electrocardiogram (ECG) signals.

8. The method of claim 7 wherein the first criterion includes the criterion that the ECG signal is not flat line.

9. The method of claim 8 wherein the first criterion includes the criterion that no QRS complexes are found in the ECG signal.

10. The method of claim 1 wherein the second set of data signals includes data signals indicative of the patient's cardiac activity.

11. The method of claim 10 wherein the second set of data signals includes electrocardiogram (ECG) signals.

12. The method of claim 1 wherein the step of commencing charging of an energy storage device upon completion of the first analysis includes charging the energy storage device to a first charge level, and wherein the step of charging the energy storage device upon completion of the second analysis to a charge level at which the device is capable of delivering the therapy comprises charging the energy storage device from the first level up to the charge level at which the device is capable of delivering the therapy.

13. The method of claim 1 wherein the step of commencing charging of an energy storage device upon completion of the first analysis includes charging the energy storage device at a first rate of charge, and further comprising the steps of performing a third analysis of a third set of data signals sensed by the medical device, if the third analysis shows the third set of data signals meets a third criterion, increasing the rate of charge.

14. The method of claim 1 wherein the process of the first analysis differs from the process of the second analysis.

15. The method of claim 1, wherein delivering the therapy comprises delivering the therapy automatically in response to the second analysis determining that the second set of data signals meet the second criterion.

16. The method of claim 1, wherein delivering the therapy comprises delivering the therapy in response to user input.

17. The method of claim 1, wherein the step of performing a second analysis comprises performing at least a portion of a second analysis after completing the first analysis.

18. The method of claim 12, wherein the first charge level is greater than a zero charge level.

19. The method of claim 12 further comprising maintaining the energy storage device at the first charge level until performing the second analysis is complete.

* * * * *